(12) United States Patent
Lyons

(10) Patent No.: US 6,516,044 B1
(45) Date of Patent: Feb. 4, 2003

(54) SCINTILLATION APPARATUS AND METHOD OF LIGHT COLLECTION FOR USE WITH A RADIATION EMITTING MEDICAL IMAGING SCANNER

(75) Inventor: Robert Joseph Lyons, Burnt Hills, NY (US)

(73) Assignee: GE Medical Systems Global Technology Co., LLC, Waukesha, WI (US)

( * ) Notice: Subject to any disclaimer, the term of this patent is extended or adjusted under 35 U.S.C. 154(b) by 53 days.

(21) Appl. No.: 09/682,842

(22) Filed: Oct. 23, 2001

(51) Int. Cl.[7] ................................................ A61B 6/00
(52) U.S. Cl. ......................... 378/19; 378/22; 250/336.1
(58) Field of Search ................... 378/19, 22; 250/336.1

(56) References Cited

U.S. PATENT DOCUMENTS

| | | | |
|---|---|---|---|
| 4,159,424 A | * | 6/1979 | Kingsley ................. 250/483.1 |
| 5,208,460 A | | 5/1993 | Rougeot et al. |
| 5,241,180 A | | 8/1993 | Ishaque et al. |
| 6,118,840 A | * | 9/2000 | Toth et al. ................... 250/367 |
| 6,359,280 B1 | * | 3/2002 | Orr et al. ................ 250/370.01 |

\* cited by examiner

*Primary Examiner*—David V. Bruce
*Assistant Examiner*—Pamela R. Hobden

(57) ABSTRACT

An improved scintillator detector cell geometry for converting radiation to light with improved light collection is provided. Shaping the exit face of a scintillator to increase the surface area of the exit face results in a decrease in a fraction of angles that undergo total internal reflection within the scintillator. The scintillator has the advantage of preventing total internal reflection parallel, as well as perpendicular, to the detecting surface of a light collection device. Further, providing a specular reflector on a hemispherical dome portion of the radiation detecting surface of the scintillator results in reduced bounce-off the specular reflector before light contacts the scintillator-photodiode interface. Furthermore, implementing a convex shape when coated with the specular reflector increases the fraction of light directed toward the photodiode compared to a plane surface parallel to the photodiode. The present invention further limits the amount of light that is trapped within the scintillator.

24 Claims, 5 Drawing Sheets

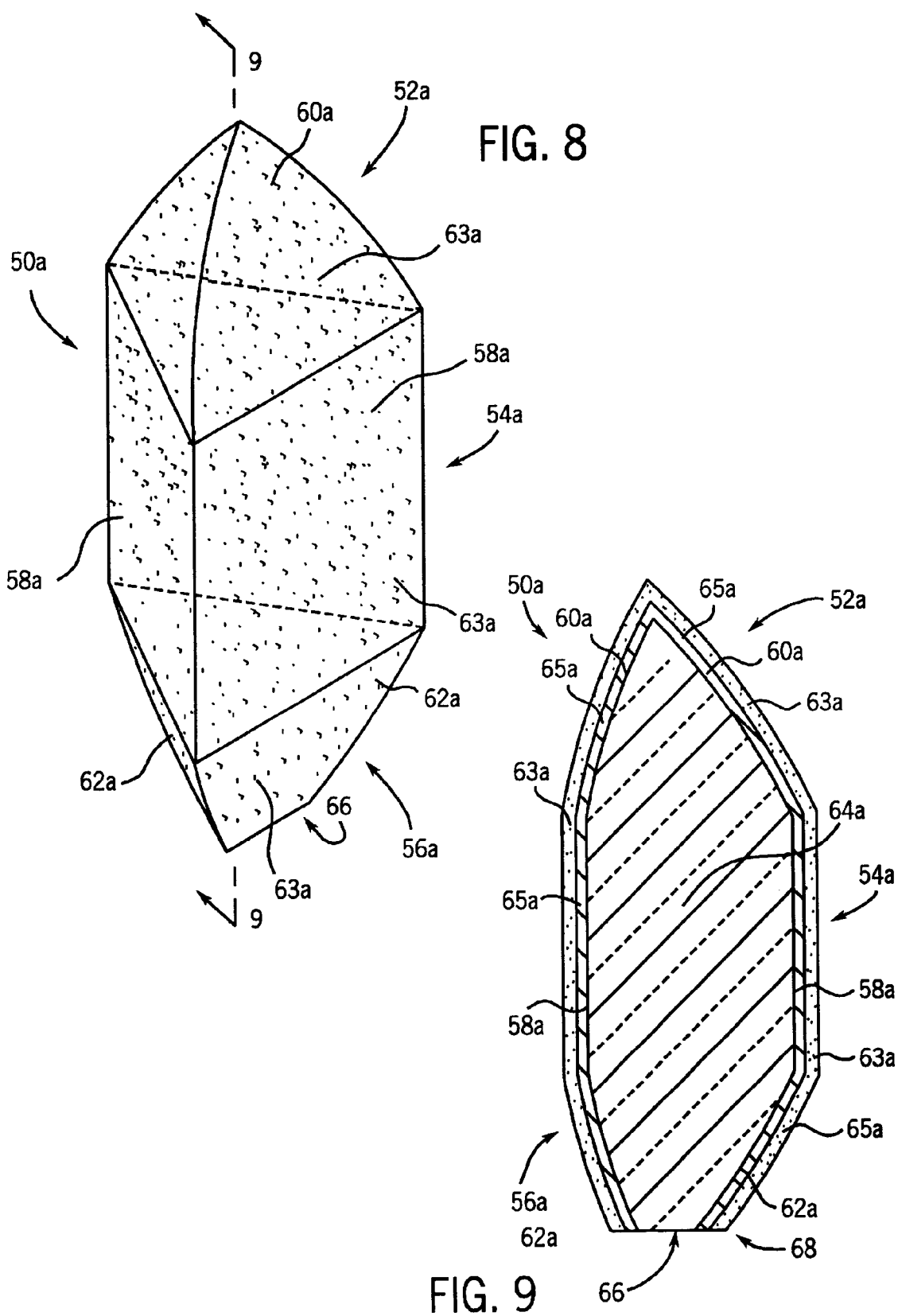

SCINTILLATION APPARATUS AND METHOD OF LIGHT COLLECTION FOR USE WITH A RADIATION EMITTING MEDICAL IMAGING SCANNER

BACKGROUND OF INVENTION

The present invention relates generally to radiation detection and, more particularly, to an improved apparatus and method of light collection for use with a radiation emitting medical imaging scanner.

Typically, in computed tomography (CT) imaging systems, an x-ray source emits a fan-shaped beam toward an object, such as a patient. The beam, after being attenuated by the object, impinges upon an array of radiation detectors. The intensity of the attenuated beam of radiation received at the detector array is typically dependent upon the attenuation of the x-ray beam by the object. Each detector element of the detector array produces a separate electrical signal indicative of the attenuated beam received by each detector element. The electrical signals are transmitted to a data processing system for analysis which ultimately results in the formation of an image.

Generally, the x-ray source and the detector array are rotated about the gantry within an imaging plane and around the object. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator.

Typically, the scintillator or scintillation detector used with CT systems and other radiation emitting medical imaging scanners are coupled to a light collection device such as a photodiode using a transparent adhesive. The transparent adhesive, however, typically limits the angles at which light can exit the scintillator to those greater than the critical angle of the interface between the scintillator and the adhesive. Moreover, scintillators usually have very high indices of refraction due to the high density required to prevent radiation leakage. As a result, an appreciable index change at the scintillator exit face occurs with resulting total internal reflection of light striking the exit face at relatively shallow angles.

Further, these known systems typically implement a rectangular block shaped scintillator to stop the radiation and maximize the area exposed. While this rectangular shape accommodates an easy to fabricate area-filling shape with the appropriate thickness for optimum radiation stopping power, the rectangular shape has several disadvantages associated with light collection by a photodiode.

For example, parallel plane walls are typically implemented that are perpendicular to the light detector photodiode thereby causing light that is emitted nearly parallel to the light collector face to bounce repeatedly off the parallel walls either by specular reflection or by total internal reflection. Moreover, there is no means of directing light preferentially toward the light detector in these rectangular shaped scintillators. Diffused reflectors have been implemented to randomize the direction of light rays, but these diffused reflectors result in the need for thicker reflectors to provide sufficient scatter by light refraction. As a result, these thicker reflectors decrease the possible re-fraction of the scintillator. Additionally, these reflectors are also not opaque so an additional opaque component to stop light leakage between cells must be employed. Other scintillators have been designed using a defused opaque coating, but the increased area of such a coating and the opportunity for multiple bounces typically results in a considerable decrease and reflectivity compared to a specular coating.

Additional disadvantages often associated with these rectangular shaped scintillators include the reflection of light back into the scintillator when the light hits the exit surface of the scintillator at an angle greater than the critical angle of the scintillator-adhesive interface. This disadvantage, as well as the previously discussed disadvantages, increase the mean number of reflections that light undergoes before striking the detector. Simply, each reflection off the side reflector of the scintillators results in a loss from the absorbance of the reflector.

It would therefore be desirable to design an apparatus and method of light collection whereby light throughput of a scintillator is increased and light collection efficiency likewise improves.

BRIEF DESCRIPTION OF THE INVENTION

The present invention is directed to improved scintillator detector cell geometry overcoming the aforementioned drawbacks. Shaping the exit face of a scintillator to increase the surface area results in a decrease in a fraction of angles that undergo total internal reflection within the scintillator. By convexly shaping the exit face, the scintillator has the advantage of preventing total internal reflection parallel, as well as perpendicular, to the detecting surface of a light collection device. Further, providing a specular reflector on a hemispherical dome portion of the radiation detecting surface of the scintillator results in reduced reflection off the specular reflector before light contacts the scintillator-photodiode interface. Furthermore, implementing a convex shape that is coated with the specular reflector, increases the fraction of light directed toward the photodiode compared to a planar surface parallel to the photodiode. The present invention further limits the amount of light that is trapped within the scintillator.

Therefore, in accordance with one aspect of the present invention, a scintillation apparatus for use with a radiation emitting medical imaging scanner is provided. The scintillation apparatus includes an entrance face configured to receive radiation and an exit face having a tetrahedral shape and configured to discharge light. The scintillation apparatus further includes a plurality of plane walls extending from the entrance face to the exit face.

In accordance with another aspect of the present invention, a CT system includes a scintillator array having a plurality of scintillation cells. Each scintillation cell of the CT system has at least one of a non-planar radiation reception surface and a non-planar light emitting surface. The non-planar reception surface and the non-planar light emitting surface are symmetrically shaped with respect to one another. The CT system further includes a radiation projection source configured to project radiation toward the scintillator array and a photodiode array having a plurality of photodiodes. The photodiode array is optically coupled to the scintillator array to detect light output therefrom. The CT system further includes a gantry having an opening to receive a subject to be scanned.

In accordance with yet another aspect of the present invention, a radiation detector for use with the radiation emitting medical imaging scanner is provided. The radiation detector includes a means for detecting radiation as well as a means for converting the radiation to light energy. The radiation detector further includes a means for emitting light energy toward a light energy detector and a means for reducing light energy bounce off within the radiation detector.

In accordance with a further aspect of the present invention, a method of light collection from a scintillation detector of a radiation emitting medical imaging scanner includes directing radiation toward a scan subject and a scintillation detector. The method further includes receiving radiation attenuated by the scan subject and converting the attenuated radiation to light energy. The light energy is then admitted through a non-planar surface of the scintillation detector. The method further includes detecting the admitted light energy from the scintillation detector.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings:

FIG. 8 is a perspective view of a scintillation cell in accordance with another alternative embodiment of the present invention.

FIG. 9 is a cross-sectional view of the scintillation cell of FIG. 8 taken along Line 9—9.

DETAILED DESCRIPTION

Figure 1:
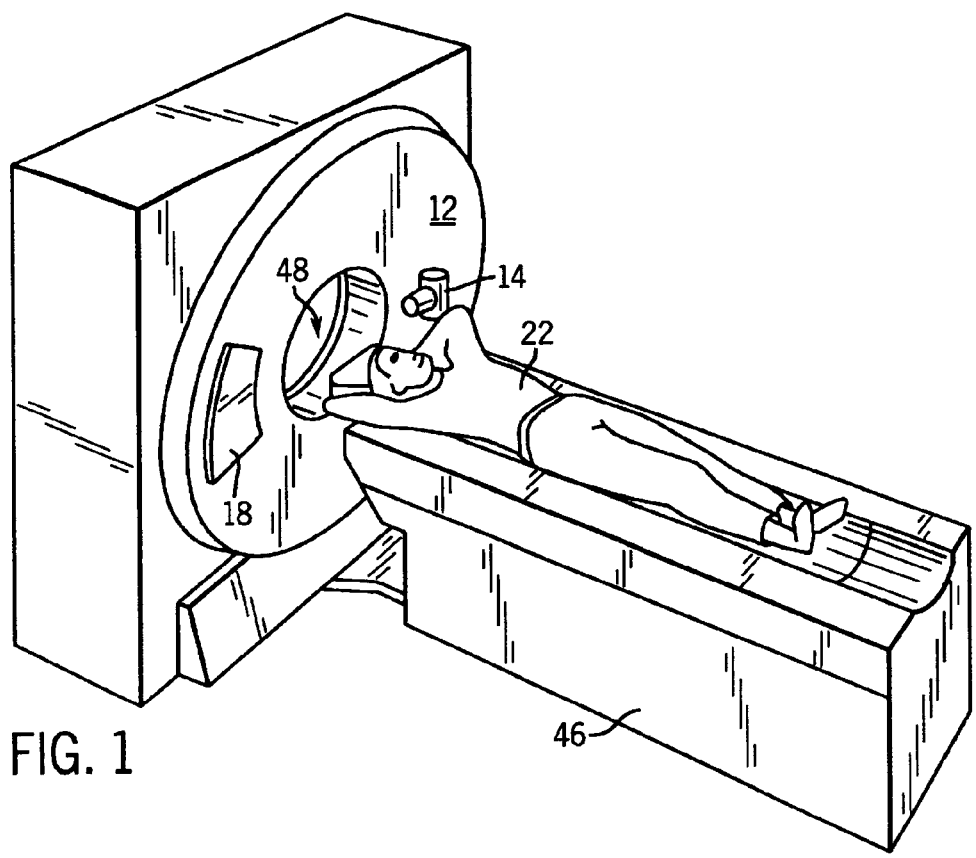
FIG. 1 is a pictorial view of a CT imaging system.
Figure 2:
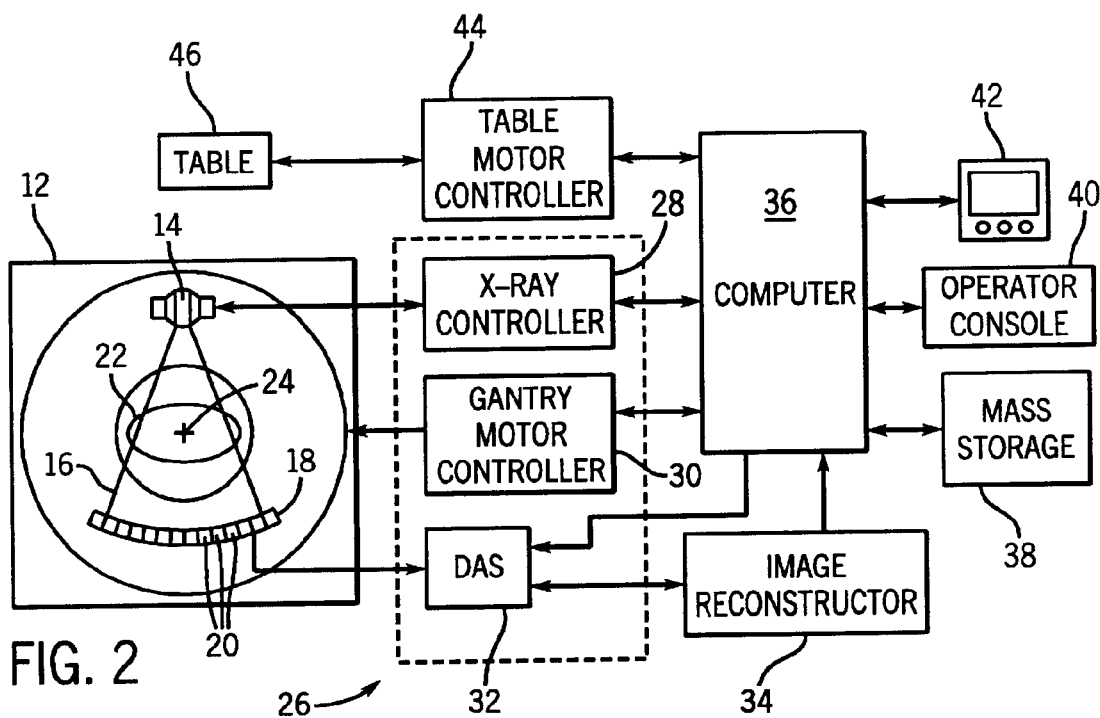
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

Figure 3:
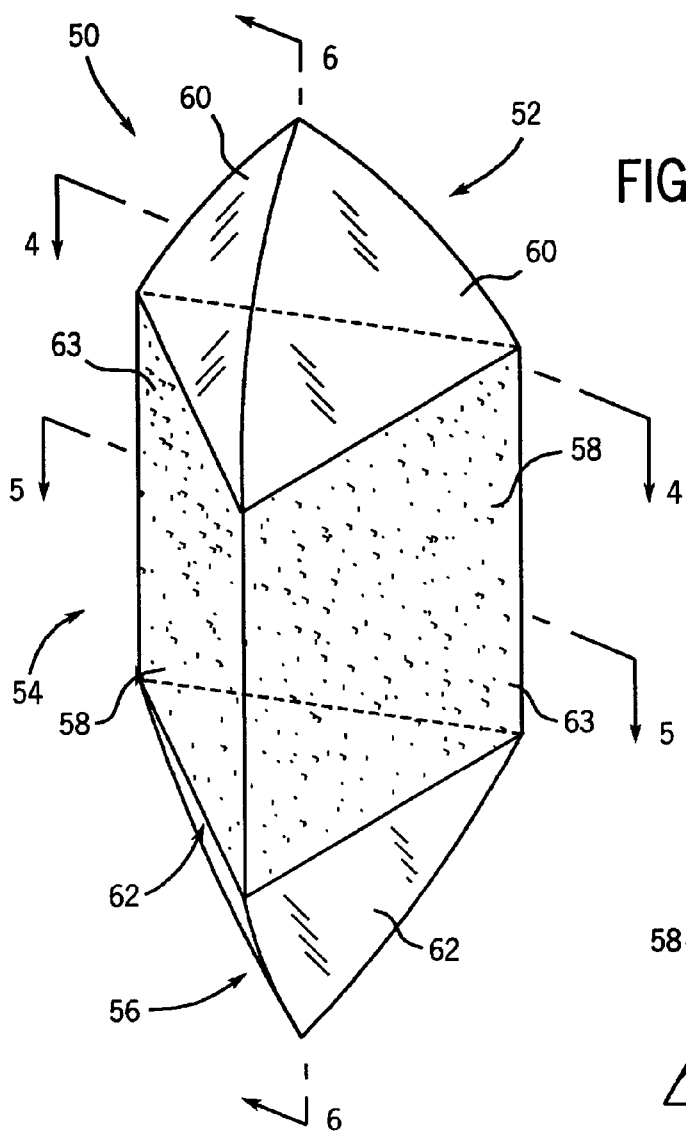
FIG. 3 is a perspective view of a scintillation detection cell in accordance with one embodiment of the present invention.

Referring now to FIG. 3, a scintillation cell 50 is shown in accordance with one embodiment of the present invention. Cell 50 includes an upper portion or radiation detection region 52, a body or intermediate region 54, and a lower portion or light emitting region 56. In this embodiment, the radiation detection region 52 as well as the light emitting region 56 have a trigonal pyramidal shape. As a result, the body 54 of cell 50 has three cell walls 58. Cell walls 58 interface with curvilinearly shaped entrance surface walls 60 at one end and interface with emitting surface walls 62 at an opposite end. In this embodiment, the scintillation cell 50 has a symmetrical shape. That is, radiation detection region 52 mirrors light emitting region 56.

FIG. 3 illustrates one preferred embodiment of the present invention having a scintillation cell with only one of a trigonal pyramidal radiation detection region 52 and a trigonal pyramidal light emission region 56. In this embodiment, the scintillation cell would have a projectionless surface at one end and a trigonal pyramidal shape at an opposite end. Further, the present invention is applicable with detection surface walls and emission surface walls that are not curvilinear in shape but rather linear. Additionally, the present invention contemplates a scintillation cell having more than three cell walls. For example, a scintillation cell with four cell walls as well as four radiation detection surface walls and four light emission surface walls are within the scope of the present invention. Also, the present invention contemplates, in an alternative embodiment, a convex or hemispherical shape for at least one of the radiation detection region and the light emission region of the scintillation cell. In this alternative embodiment, the convex radiation detection region and the convex light emission region would each have a circular cross-section.

Figure 4:
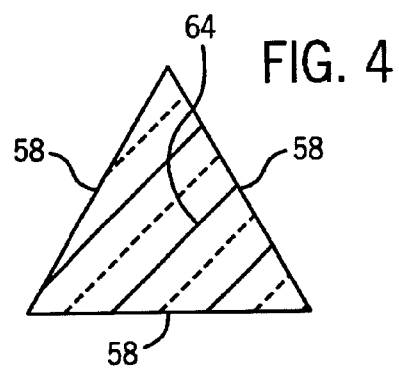
FIG. 4 is a cross-sectional view of a top portion of the scintillation cell of FIG. 3 taken along line 4—4.

Referring to FIG. 4, a cross-sectional view taken along line 4—4 of FIG. 3 illustrates the triangular cross-section of the preferred embodiment shown in FIG. 3. FIG. 4 illustrates the triangular orientation of the interface between the radiation detection region 52 and the intermediate or body region 54. As shown, three cell walls are shown. The cell walls 58 are formed of and enclose scintillation materialwhich, as indicated previously, is designed to convert high frequency electromagnetic energy such as x-rays or gamma rays to light.

Figure 5:
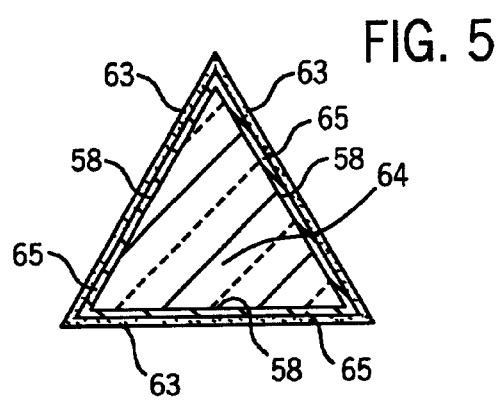
FIG. 5 is a cross-sectional view of the scintillation cell of FIG. 3 taken along line 5—5.

FIG. 5 is a cross-sectional view of the scintillation cell shown in FIG. 3 taken along line 5—5 thereof. As shown and similar to FIG. 4, FIG. 5 illustrates the triangular orientation of the scintillation cell 50. Three cell walls 58 formed of scintillation material intersect to form a triangular body and enclose scintillation material 64. FIG. 5 also illustrates the position of a reflective coating 63 about the periphery of cell walls 58. Interposed between the optically reflective layer 63 and the cell walls 58 is a dielectric layer 65. The dielectric layer 65 is formed of a dielectric selected to have an optical index that is less than that of the material forming the scintillator. A number of dielectric materials such as clean air may be used if they have an optical index less than that of the scintillator material 64. The dielectric layer 65 operates to reflect light photons generated by the scintillation material 64 back into the scintillator body thereby increasing light collection efficiency. The dielectric layer 65 operates to increase the number of light photons that eventually exit the light emitting region 56, FIG. 5 and strike the photodetector 20, FIG. 2.

Still referring to FIG. 5, reflective coating 63 is disposed around the periphery of the dielectric layer 65. Light photons that strike the interface between cell walls 58 and the dielectric layer 65 at greater than the critical angle for that interface will pass through the dielectric layer 65 and preferably strike reflective layer 63. Reflective layer 63 will reflect the light photons back through the dielectric layer 65 and into the scintillation material 64. In a preferred embodiment, the optically reflective layer 63 has a specular surface and includes a metal having a relatively high reflectance.

Figure 6:
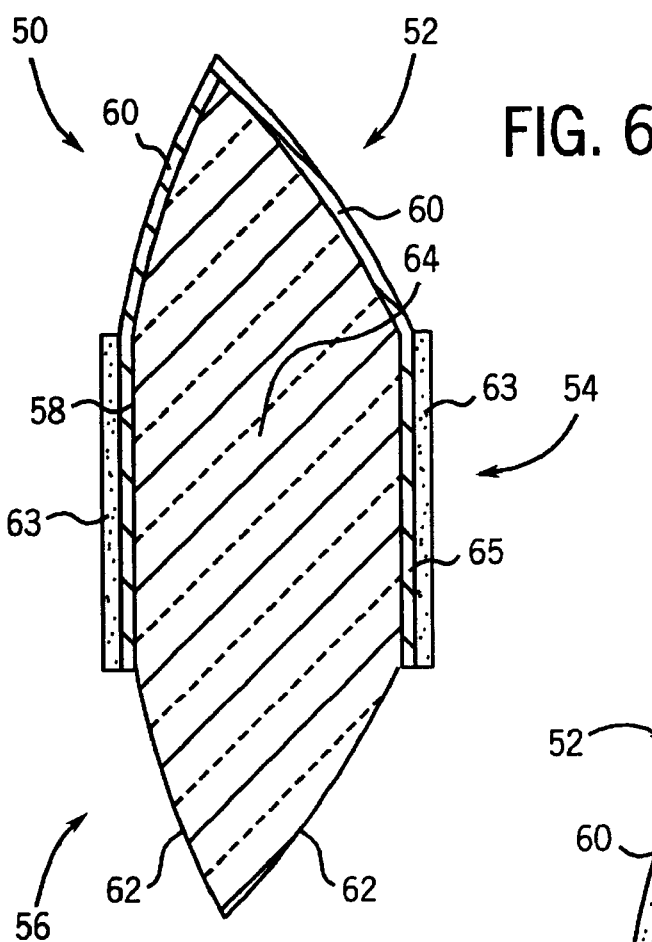
FIG. 6 is a vertical cross-sectional view of the scintillation cell of FIG. 3 taken along line 6—6.

FIG. 6 is a cross-sectional view of the scintillation cell 50 taken along line 6—6 of FIG. 3. As shown, scintillation cell 50 has a tetrahedral radiation detection region 52 and a tetrahedral light emitting region 56 with the body or intermediate region 54 therebetween. Each region 52, 54, 56 of cell 50 is formed of a solid scintillation material 64. X-rays or gamma rays detected by the radiation surface as defined by walls 60 are converted to light by the scintillation material 64 in accordance with known conversion techniques. The light photons are eventually then admitted through the light emission region 56 and detected by a photodetector. Utilizing a tetrahedral or pyramidal shape at the detection region 52 creates a significant directional component within the scintillation cell 50. Simply, the portion of the light photons generated within the scintillation cell 50 that are directed back toward the radiation detection surface 60 may be, in accordance with the present invention, reflected toward the light emission region 56 such that the number of reflections off the interior surfaces of the scintillation cell are reduced. That is, the present invention reduces the number of parallel plane surfaces within the scintillation cell. As a result, light emitted nearly perpendicular to the plane surfaces are less susceptible to being caught in an optical cavity within the scintillation cell. The pyramidal shape of the detection region 52 improves the light photons progress toward the light emission region and further implementing a specular reflector 65 and a dielectric layer 63 along a periphery of the side walls 58 of the scintillation cell 50 also improves light direction toward the light emitting surface.

By shaping the light emitting region 56 in a tetrahedral or pyramidal shape increases the surface area of the light emitting region 56 but also decreases the fraction of angles that undergo total internal reflection within the scintillation cell 50. Maximized light throughput is possible with a trigonal pyramidal shape and has the advantage of preventing total internal reflection parallel as well as perpendicular to the light emitting surface. While the light emitting region 56 may have any convex shape or series of shapes, all of which are within the scope of the present invention, the use of multiple protrusions, i.e., ripples, from the light emitting surface can be problematic since the light exiting one protrusion may be refracted back into the scintillator by a neighboring protrusion thereby jeopardizing the light collection efficiency of the scintillator cell and the photodetector.

Figure 7:
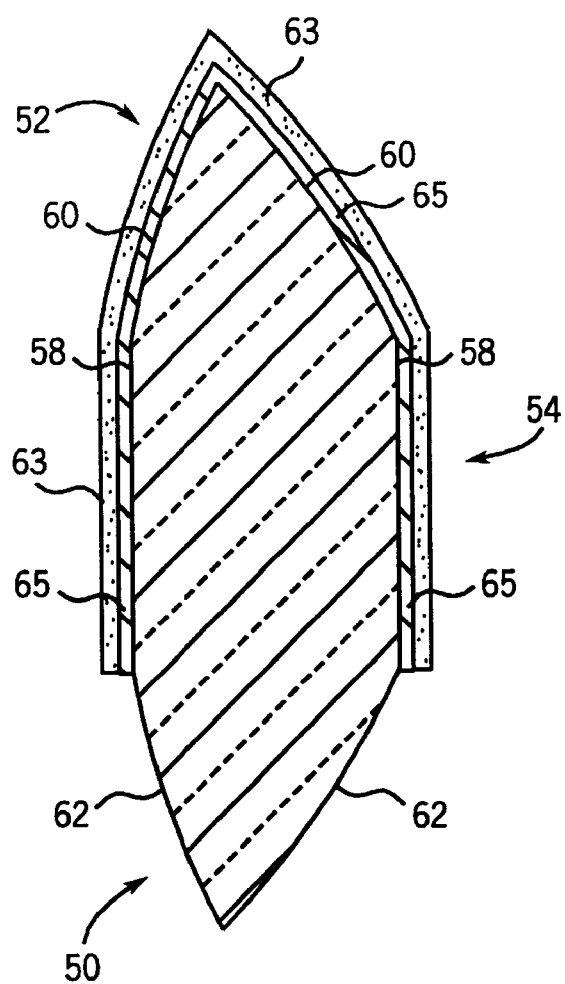
FIG. 7 is a cross-sectional view similar to that shown in FIG. 6 illustrating a same alternative embodiment or different alternative embodiment of the present invention.

FIG. 7 is a cross-sectional view similar to that shown in FIG. 6 showing one alternate embodiment of the present invention. In this embodiment, a reflective coating extends along a portion of the periphery of the scintillation cell 50. Whereas in the embodiment of FIG. 6, the reflective coating 63 extended only along an outer periphery of the intermediate region 54, in the embodiment of FIG. 7, the reflective coating 63 is implemented along the intermediate side walls 58 as well as the detection surface side walls 60 and the light emission surface side walls 62. In another alternative embodiment, the reflective coating may be extended to align along a portion of the periphery (not shown) of the light emitting region. Coating a portion of the exterior of the scintillator cell 50 with a reflective coating 63 represents only one preferred embodiment of the present invention. That is, a reflective coating may be implemented along an outer periphery of the side walls of the scintillation cell 50 as shown in FIG. 6 or, in another alternative, the reflective coating 63 may be used along an outer periphery of one or both of radiation detection region or the light emission region 56.

Referring to FIG. 8, another alternative embodiment of the present invention is shown, similar to that shown in FIG. 3, which will be described using like numerals and a parenthetical (a) in describing the features thereof. As shown, scintillation cell 50(a) is a three-sided structure having three body side walls 58(a) and a trigonal pyramidal upper region 52(a) and a trigonal pyramidal lower region 56(a). Scintillator 50(a) is different from scintillator 50 shown in FIG. 3 in two respects. First, scintillation cell 50(a) has a flat light emission surface 66. The light emission surface 66 is flat to ensure a greater connection to a photodetector (not shown). Secondly, the scintillation cell 50(a) includes a reflective coating 63(a) along the entire periphery except for the flat light emission surface 66. As indicated previously, the reflective coating layer 63(a) improves the light collection within the scintillation cell by reducing light photon bounce-off within the scintillation cell. Further, the reflective coating 63(a), such as a specular reflector, may also prevent radiation that penetrates between adjacent scintillation cells from reaching the photo detector.

A cross-sectional view taken along line 9—9 of FIG. 8 is shown in FIG. 9. As may be readily seen, the scintillation cell 50(a) has a conical radiation detection region 52(a) as well as a planar-bottomed trigonal pyramidal light emission region 56(a). As shown, the light emission surface 66 extends horizontally across a tapered region 68 of light emission region 56(a).

Figure 10:
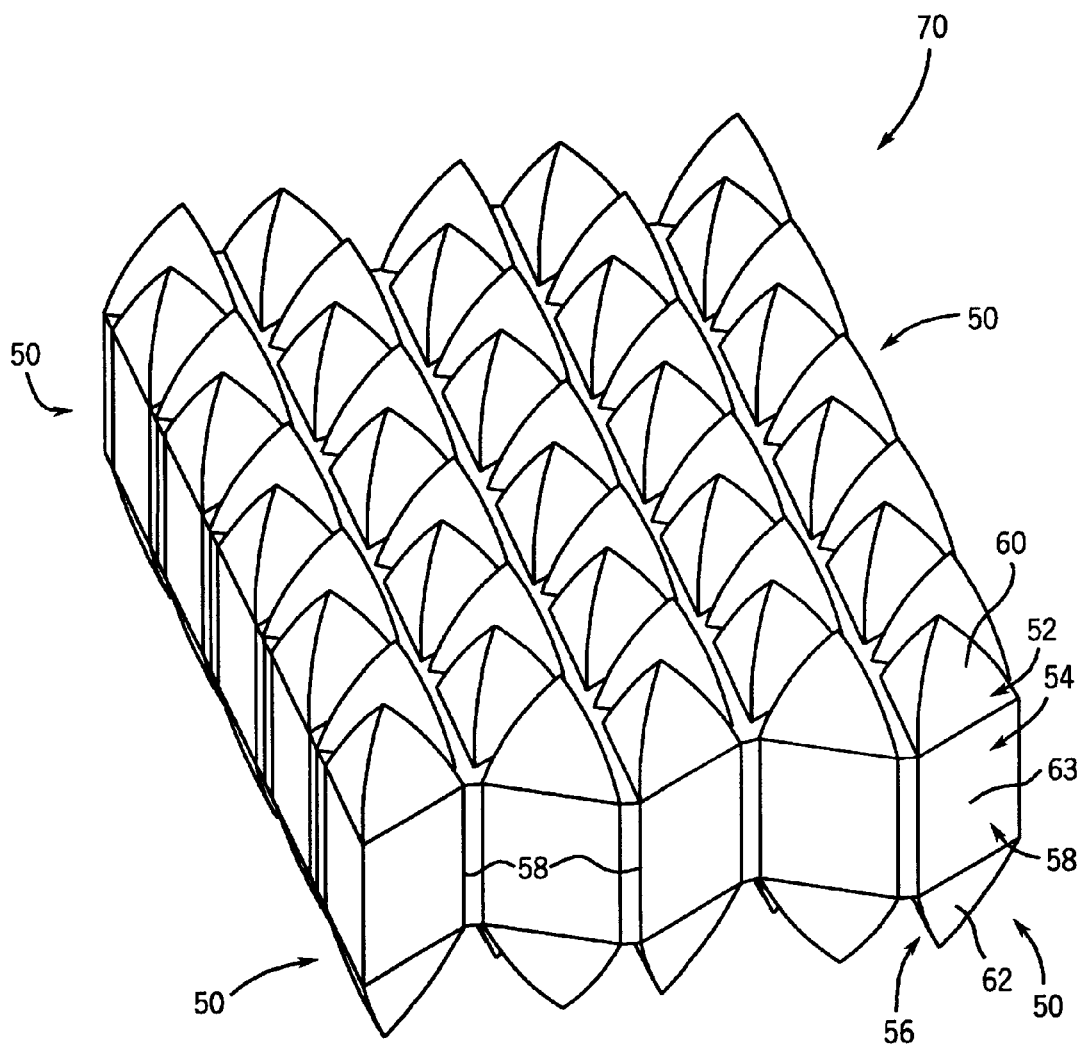
FIG. 10 is a perspective view of a portion of a scintillator array incorporating a plurality of the scintillation cells shown in FIG. 3.

FIG. 10 illustrates a portion of a scintillator array incorporating a plurality of the scintillation cell 50 shown in FIG. 3. Scintillator array 70 includes a plurality of scintillation cells wherein each scintillation cell 50 has a trigonal pyramidal radiation detection region 52 and a trigonal pyramidal light emission region 56 and three side walls 58 of an intermediate region 54 therebetween. Radiation is detected by each scintillation cell 50 of scintillator array 70 and converted to light energy which is then detected by a photodiode array (not shown) coupled to the scintillator array 70. Specifically, each photodiode (not shown) of the photodiode array is coupled to a corresponding scintillation cell 50 of the scintillator array 70. As indicated previously, the light energy generated by each scintillation cell 50 and detected by each photodiode (not shown) is indicative of the x-rays attenuated by an imaging subject and detected by the scintillator array 70. Each photodiode detects light and transmits an electrical signal to a data acquisition system, FIG. 2, for subsequent processing and image reconstruction.

Accordingly, in accordance with one embodiment of the present invention, a scintillation apparatus for use with a radiation emitting medical imaging scanner is provided. The scintillation apparatus includes an entrance, the entrance face configured to receive radiation, and an exit face having a tetrahedral shape and configured to discharge light. The scintillation apparatus further includes a plurality of plane walls extending from the entrance face to the exit face.

In accordance with another embodiment of the present invention, a CT system includes a scintillator array having a plurality of scintillation cells. Each scintillation cell of the CT system has at least one of a non-planar radiation reception surface and a non-planar light emitting surface. The CT system further includes a radiation projection source configured to project radiation toward the scintillator array and a photodiode array having a plurality of photodiodes. The photodiode array is optically coupled to the scintillator array to detect light output therefrom. The CT system further includes a gantry having an opening to receive a subject to be scanned.

In accordance with yet another embodiment of the present invention, a radiation detector for use with the radiation emitting medical imaging scanner is provided. The radiation detector includes a means for detecting radiation as well as a means for converting the radiation to light energy. The radiation detector further includes a means for emitting light energy toward a light energy detector and a means for reducing light energy bounce off within the scintillator.

The present invention has been described in terms of the preferred embodiment, and it is recognized that equivalents, alternatives, and modifications, aside from those expressly stated, are possible and within the scope of the appending claims.

What is claimed is:

1. A scintillation apparatus for use with a radiation emitting medical imaging scanner, the scintillation apparatus detector comprising:
    an entrance face, the entrance face configured to receive radiation;
    an exit face, the exit face having a tetrahedral shape and configured to emit light; and
    a plurality of plane walls extending from the entrance face to the exit face.

2. The scintillation apparatus of claim 1 further comprising a specular reflector extending along a periphery of the plurality of plane walls and between the entrance face and the exit face.

3. The scintillation apparatus of claim 1 wherein the entrance face has a convex shape and the exit face has a trigonal pyramidal shape.

4. The scintillation apparatus of claim 3 wherein the entrance face has a trigonal pyramidal shape.

5. A CT system comprising:
    a scintillator array having a plurality of scintillation cells, each scintillation cell having at least one of a non-planar radiation reception surface and a non-planar light emitting surface wherein the non-planar radiation reception surface and the non-planar light emitting surface are symmetrically shaped;
    a radiation projection source configured to project radiation toward the scintillator array;
    a photodiode array having a plurality of photodiodes, the photodiode array being optically coupled to the scintillator array to detect light output therefrom; and
    a gantry having an opening to receive a subject to be scanned.

6. The CT system of claim 5 wherein each of the non-planar radiation reception surface and the non-planar light emitting surface has a convex shape.

7. The CT system of claim 6 wherein each of the non-planar radiation reception surface and non-planar light emitting surface has a conical shape.

8. The CT system of claim 6 wherein each of the non-planar radiation reception surface and the non-planar light emitting surface has a trigonal pyramidal shape.

9. The CT system of claim 5 wherein each scintillation cell comprises a plurality of cell walls extending from the non-planar radiation reception surface to the non-planar light emitting surface, the plurality of cell walls having a portion thereof extending convergently to a corresponding photodiode scintillator interface.

10. The CT system of claim 9 wherein each scintillation cell further comprises a specular reflector coupled to a non-convergent portion of the plurality of cell walls.

11. The CT system of claim 9 wherein each scintillation cell has three cell walls and a reflective coating affixed to an outer periphery of each cell wall.

12. The CT system of claim 5 wherein each scintillation cell comprises a reduced light trapping area.

13. A radiation detector for use with a radiation emitting medical imaging scanner, the scintillator comprising:
    a non-planar means for detecting radiation;
    means for converting the radiation to light energy;
    a non-planar means for emitting light energy toward a light energy detector; and
    means for reducing light energy bounce off within the scintillator, said means including a reflecting coating affixed to at least one of the non-planar means.

14. The radiation detector of claim 13 further comprising means for directing light energy toward the non-planar means for emitting, the means for directing having means for reducing light energy therethrough.

15. The radiation detector of claim 13 further comprising means for decreasing a number of light emission angles that undergo total internal reflection.

16. The radiation detector of claim 15 further comprising means for increasing a number of light emission angles.

17. A method of light collection from a scintillation detector of a radiation emitting medical imaging scanner, the method comprising:
    directing radiation toward a scan subject and a scintillation detector, the scintillation detector having a pyramidal detection surface;
    receiving radiation attenuated by the scan subject;
    converting the attenuated radiation to light energy;
    emitting the light energy through a surface of the scintillation detector; and
    detecting the emitted light energy.

18. The method of claim 17 wherein the light emission surface is convexly oriented.

19. The method of claim 18 wherein the light emission surface has one of a hemispherical shape, a conical shape, and a trigonal pyramidal shape.

20. The method of claim 17 wherein at least one of the radiation receiving surface and the light emitting surface has a specular reflector coating affixed thereto.

21. The method of claim 17 further comprising decreasing a number of light emission angles susceptible to total internal reflection.

22. The method of claim 17 further comprising eliminating radiation penetration between adjacent scintillation detectors.

23. The method of claim 17 further comprising preventing total internal reflection in a direction parallel to the non-planar detection surface of the scintillation detector.

24. The method of claim 17 further comprising preventing total internal reflection in a direction perpendicular to the non-planar detection surface of the scintillation detector.

* * * * *